United States Patent [19]

Pillsbury

[11] Patent Number: 4,526,724

[45] Date of Patent: Jul. 2, 1985

[54] PROCESS FOR THE PREPARATION OF ZERO VALENT BIS-ARENE TRANSITION METAL COMPOUNDS

[75] Inventor: Dale G. Pillsbury, Elburn, Ill.

[73] Assignee: Standard Oil Company (Indiana), Chicago, Ill.

[21] Appl. No.: 537,840

[22] Filed: Sep. 30, 1983

[51] Int. Cl.$^3$ .......................... C07F 9/00; C07F 7/28; C07F 11/00
[52] U.S. Cl. ...................................... 556/43; 556/52; 556/58; 556/140; 534/14
[58] Field of Search ...... 260/429 AR, 429.5, 438.5 R, 260/429 R

[56] References Cited

U.S. PATENT DOCUMENTS

| | | | |
|---|---|---|---|
| 2,818,416 | 12/1957 | Brown et al. | 260/429 AR |
| 2,892,857 | 6/1959 | Ecke et al. | 260/429 R |
| 2,953,586 | 9/1960 | Hafner et al. | 260/429 R |
| 3,129,237 | 4/1964 | Hess et al. | 260/429 AR |
| 3,906,017 | 9/1975 | Middleton et al. | 260/429 AR |
| 4,333,881 | 6/1982 | Greco et al. | 260/429.5 X |

Primary Examiner—Helen M. S. Sneed
Attorney, Agent, or Firm—William H. Magidson; William T. McClain; Ralph C. Medhurst

[57] ABSTRACT

An improved process for the preparation of zero valent bis-arene transition metal compounds comprises reducing bis-arene transition metal (I) compound with a high-electropositive metal in an ether solvent at reflux temperature.

10 Claims, No Drawings

PROCESS FOR THE PREPARATION OF ZERO VALENT BIS-ARENE TRANSITION METAL COMPOUNDS

BACKGROUND OF THE INVENTION

This invention relates to a process for the preparation of zero valent bis-arene transition metal compounds. More particularly, the present invention comprises the reduction of a bis-arene transition metal (I) compound with a highly-electropositive metal of Group IA or IIA of the Periodic Table of Elements in a substantially anhydrous ether solvent.

Zero valent bis-arene transition metal compounds are known in the art. Many of these compounds, and methods for their preparation, are disclosed in the comprehensive study of bis-arene transition metal complexes by W. E. Silverthorn, Adv. Orgmet. Chem., 13, pp. 47–137 (1975) and the references cited therein. The Silverthorn article and references therein are incorporated herein by reference. It is generally recognized that a zero valent bis-arene transition metal compound has the following structural formula:

$$[(Arene)_2M]°$$

wherein M represents a transition metal and arene represents an aromatic hydrocarbon containing at least one six-membered ring pi-bonded to said transition metal.

α-Olefin polymerization catalysts containing zero valent bis-arene transition metal compound are also known in the art. U.S. Pat. No. 3,123,571 (Darrell W. Walker et al.) and U.S. Pat. No. 3,157,712 (Darrell W. Walker, et al.), incorporated herein by reference, describe the use of a number of zero valent bis-arene transition metal compounds in catalyst compositions for polymerization of olefins. Polymerization of ethylene using zero valent bis-benzenechromium in the presence of oxygen is described by H. Yamazaki et al., Mem. Inst. Sci. and Ind. Res., Osaka Univ., 20, p. 107 (1968). This article is also incorporated herein by reference.

Various methods for the preparation of zero valent bis-arene metal compounds are described in the aforementioned Silverthorn article and references therein. Two appear to have gained wider application than the other methods.

The first method is a two-step wet chemical synthesis comprising (1) formation of bis-arene transition metal (I) compound wherein the metal is in 1+ valence state by reacting transition metal halide, an arene, aluminum trihalide and aluminum metal, and (2) hydrolyzing the reaction product to yield zero valent bis-arene transition metal compound. The hydrolysis step involves disproportionation of the bis-arene transition metal (I) compound to the desired zero valent bis-arene transition metal compound, and transition metal compound wherein the transition metal is in 2+ or 3+ valence state, depending on the pH of the solution. Disproportionation of the bis-arene transition metal (I) compound can be represented by the following reactions:

$$2[(Arene)_2M]^+ \xrightarrow{H_2O}_{\text{neutral medium}}$$

$$[(Arene)_2M]° + M^{2+} + 2 \text{ Arene}$$

$$3[(Arene)_2M]^+ \xrightarrow{H_2O}_{\text{alkaline medium}}$$

$$[2(Arene)_2M]° + M^{3+} + 2 \text{ Arene}$$

wherein M represents a transition metal.

Although this method is widely used, its disadvantages are that it involves many manipulations of very air-sensitive compounds and the maximum theoretical yield of zero valent bis-arene transition metal compound is about 67%, based on the transition metal, due to the disproportionation. Thus, about one-third of the transition metal is not utilized for the production of zero valent bis-arene transition metal compound in this method.

Preparation of various zero valent bis-arene transition metal compounds by this method is described in the aforementioned Silverthorn study, and references therein, and particularly in F. Calderazzo, Inorg. Chem., 3, 810(1964); E. O. Fischer and J. Seeholzer, Z. Anorg. Allgem. Chem., 312, 244(1961); E. O. Fisher and A. Rechziegel; Chem. Ber., 94, 2204(1961); F. Hein and K. Kortte, Z. Anorg. Allgem. Chem., 307, 52(1960); E. O. Fischer et al., Chem. Ber., 93, 2065(1960); and E. O. Fischer and H. Kogler, Chem. Ber., 90, 250(1957).

The second method is metal vapor synthesis which involves direct condensation of transition metal atoms are arene at liquid nitrogen temperature to produce zero valent bis-arene transition metal compound. Compounds, such as zero valent bis-benzene titanium and zero valent bis-(hexafluorobenzene)chromium, which were not accessible by the aforementioned two-step wet chemical synthesis, have been prepared by this method. However, this method is unsuitable for the preparation of bis-arene compounds of transition metals of the second- and third-row of the Periodic Table, because of much lower volatility of these metals. Accordingly, there is a need for an improved process for the preparation of zero valent bis-arene transition metal compounds.

Preparation of various zero valent bis-arene transition metal compounds by metal vapor synthesis is also described in the aforementioned Silverthorn study and references therein, and particularly in F. W. S. Benfield et al., J. Chem. Soc. Chem. Commun., 866(1973); R. Middleton, J. Chem. Soc., Dalton Trans. 120(1973); and P. S. Skell, J. Amer. Chem. Soc., 95, 3337(1973).

The general object of this invention is to provide an improved synthesis of zero valent bis-arene transition metal compounds. Another object is to provide an improved yield of the desired zero valent bis-arene transition metal compounds. Other objects appear hereinafter.

SUMMARY OF THE INVENTION

Zero valent bis-arene transition metal compounds can be prepared by the reduction of bis-arene transition metal (I) compound with a highly-positive metal of Group I or II of the Periodic Table of Elements in a substantially anhydrous ether solvent. This invention is simple chemical synthesis which provides better yields of the desired zero valent bis-arene transition metal compound, since the theoretical yield is not limited to about a 67% level of the known process due to the fact that no hydrolytic disproportionation of the bis-arene transition metal (I) compound occurs. It was discovered that the reduction of bis-arene transition metal (I) compound proceeds only in an ether solvent such as tetrahydrofuran. If a highly-electropositive metal of Group IA or IIA of the Periodic Table, such as magnesium metal, is added alone, no reaction occurs even after refluxing the reaction mixture for many hours. It is believed that the role of the ether solvent is two-fold. First, to lower the redox potential of aluminum trihalide, when present in the reaction medium, which has been established to be an oxidant toward zero valent bis-arene transition metal compound, and second, to bind the magnesium cation.

BRIEF DESCRIPTION OF THE INVENTION

The present invention comprises the reduction of bis-arene transition metal (I) compound with highly-electropositive metal of Group I or II of the Periodic Table of Elements in the presence of a substantially anhydrous ether solvent to produce a zero valent bis-arene transition metal compound. The reduction is carried out in an inert atmosphere at elevated temperature.

DETAILED DESCRIPTION OF THE INVENTION

The present invention provides a simple synthesis of zero valent bis-arene transition metal compounds.

Briefly, bis-arene transition metal (I) compound, prepared according to known methods, is reduced with a highly-electropositive metal of Group IA or IIA of the Periodic Table of Elements in the presence of a substantially anhydrous ether solvent to yield the corresponding zero valent bis-arene transition metal compound.

The term transition metal as used herein embraces metals of Group IV to Group VIII of the Periodic Table of Elements, particularly titanium, zirconium, vanadium, niobium, chromium, molybdenum, manganese, technetium, iron, cobalt and nickel.

The term arene, as used herein, means an aromatic hydrocarbon containing at least one six-membered ring pi-bonded to the transition metal. The arene includes benzene; benzene substituted with one or more alkyl groups containing from 1 to 6 carbon atoms, such as toluene, xylene, durene, 1,3,5-trimethylbenzene, hexamethylbenzene, ethylbenzene, ethylbenzene, 1,3,5-triethylbenzene, isopropylbenzene and the like; naphthalene; and anthracene.

The term ether solvent, as used herein, embraces an ether and a mixture of an ether and a hydrocarbon solvent.

Suitable ethers include tetrahydrofuran, dioxan, lower (2 to 8 carbon atoms) dialkyl ethers, such as diethyl ether, dipropyl ether, dibutyl ether, dipentyl ether, dihexyl ether, and the like; alkylvinyl and lower (2 to 8 carbon atoms) alkyl-allyl ethers such as ethyl-, propyl-, butyl-, pentyl-, and hexylvinyl, and hexylallyl ethers, alkaryl ethers, such as anisole, propylphenyl ether, and the like; arylvinyl and arylallyl ethers, such as phenyvinyl ether and phenylallyl ether; and diaryl ethers. Tetrahydrofuran is particularly suitable ether because of higher reduction rate in its presence.

Suitable hydrocarbon solvents in the mixture with an ether include liquid aliphatic alkanes and cycloalkanes, such as pentane, hexane, heptane and cycloalkane; and aromatic hydrocarbons, such as benzene, toluene and xylene.

Useful highly-electropositive metals include Group IA and IIA metals of the Periodic Table of Elements, such as lithium, sodium, potassium, magnesium, calcium, and strontium. Magnesium is preferred because of its strong reducing activity. When magnesium is employed, it may be desirable to pretreat it, in the conventional manner, to remove an oxide layer formed on its surface on prolonged standing, thereby increasing its activity by treating magnesium with a lower alkane dihalide, such as 1,2-dibromoethane and 1,2-dichloroethane.

The reduction is carried out in the atmosphere of an inert gas because of sensitivity of both bis-arene transition metal (I) compound and zero valent bis-arene transition metal compound to air. Suitable inert gas includes nitrogen and a noble gas, such as helium, neon, argon, krypton, and xenon.

The reactants are employed in amounts such that the ratio of transition metal halide to aluminum metal is $\leq 1.5:1$ and the ratio of transition metal halide to Group IA or IIA metal is $\leq 2:1$.

The reaction temperature is not critical and depends upon specific solvent employed and pressure at which the reaction is conducted. Conveniently, the reaction is conducted at a temperature from about room temperature to about 150° C. The preferred reaction temperature is the reflux temperature of the ether solvent at the pressure employed because the reaction proceeds with greater speed.

The reaction time is not critical and can be from several hours to several days.

The process of the present invention can be used to prepare the following zero valent bis-arene transition metal compounds: dibenzene titanium, dibenzene vanadium, dibenzene chromium, dibenzene molybdenum, dibenzene iron, dibenzene cobalt, dibenzene technetium, bis(o-, m-, or p-toluene)chromium, bis(o-, m-, or p-toluene)molybdenum, bis(o-, m-, or p-toluene)vanadium, bis(o-, m-, or p-ethylbenzene)chromium, bis(o-, m-, or p-ethylbenzene)molybdenum, bis(o-, m-, or p-ethylbenzene)vanadium, bis(o-, m-, or p-isopropylbenzene)chromium, bis(o-, m-, or p-isopropylbenzene)molybdenum, bis(o-, m-, or p-isopropylbenzene)vanadium, bis(1,3-dimethylbenzene)vanadium, bis(1,3-diisopropylbenzene)chromium, bis(1,3-diisopropylbenzene) bis(1,3-diisopropylbenzene)vandium, bis(1,3,5-trimethylbenzene)chromium, bis(1,3,5-trimethylbenzene)molybendum, bis(1,3,5-trimethylbenzene)vanadium, bis(1,3,5-triethylbenzene)chromium, bis(1,3,5-triethylbenzene)molybdenum, bis(1,3,5-triethylbenzene)vanadium, bis(hexamethylbenzene)chromium, bis(hexamethylbenzene) molybdenum, bis(hexamethylbenzene)vanadium, bis(naphthalene)chromium, bis(naphthalene)molybdenum, bis(naphthalene)vanadium, bis(anthracene)chromium, bis(anthracene)molybdenum, bis(anthracene)vanadium and the like.

The following examples are given for the purpose of further illustrating the present invention and are not intended in any way to limit the scope of the invention.

EXAMPLE 1

20 grams of vanadium trichloride, 3.45 grams of aluminum powder, 33.9 grams of anhydrous aluminum chloride and 200 milliliters of dry 1,3,5-trimethylbenzene were added to the reaction vessel equipped with a stirrer, reflux condenser and a thermometer. The reaction mixture was refluxed and vigorously stirred at the temperature of about 130° C. to 134° C. for about 3 hours in an inert atmosphere of argon. Then, the mixture was cooled to room temperature and 15.5 grams of magnesium powder were added to the mixture. The resulting mixture was heated under refluxing conditions for about 24 hours and cooled to room temperature. A sample of the reaction mixture was subjected to thin layer chromatography on degassed alumina, eluted with a 1:1 heptane/benzene solvent for evidence of any reaction. No reaction was evidenced. 250 milliliters of freshly-distilled dry tetrahydrofuran were then added to the reaction mixture, and the mixture was heated. The mixture was refluxed or about four and a half days, cooled to room temperature, filtered, and the residue washed several times with portions of 1,3,5-trimethylbenzene. The filtrate and washings were combined and concentrated to a semi-solid in vacuum. The semi-solid was taken up in heptane, filtered, and passed through a column of degassed calcined alumina. The eluate from the column was concentrated by heating on a hot plate, then cooled to yield zero valent bis(1,3,5-trimethylbenzene)vanadium. The obtained compound exhibited an infrared spectrum and a thin layer chromatogram consistent with that of the zero valent bis(1,3,5-trimethylbenzene)vanadium obtained by the known disproportion method.

EXAMPLE 2

20 grams of vanadium trichloride, 32.8 grams anhydrous aluminum chloride, 3.2 grams of aluminum powder and 500 milliliters of benzene were added to a reaction vessel equipped with a stirrer, a reflux condenser and a thermometer. The reaction mixture was vigorously stirred and refluxed for about thirty hours in an inert atmosphere or argon, then cooled to room temperature. To the resulting mixture were then added, dropwise, 30 milliliters of freshly-distilled tetrahydrofuran, followed by the addition of a slurry of activated magnesium prepared by reacting 45 grams of magnesium, 80 milliliters of tetrahydrofuran and 16 milliliters of 1,2-dichloroethane. The mixture was refluxed in an atmosphere of argon for about three days, cooled to room temperature, and the volume reduce to about 100 milliliters. Then, 200 milliliters of heptane were added, the mixture stirred, and the solvent removed until practically dry. An additional amount of heptane was then added, the mixture stirred and filtered. The residue was washed with benzene portions, the washings combined with the filtrate, and the solvent removed to yield zero valent dibenzene vanadium as a crystalline solid having infrared spectrum peaks at 988 cm$^{-1}$, 957 cm$^{-1}$, and 742 cm$^{-1}$, which are consistent with those of the dibenzene vanadium compound obtained by the known process.

What is claimed is:

1. A process for the preparation of a zero valent bis-arene transition metal compound which comprises reducing a bis-arene transition metal (I) compound with a highly-electropositive metal of Group IA or IIA of the Periodic Table of Elements in a substantially anhydrous ether solvent in a substantially inert atmosphere.

2. The process of claim 1 wherein said ether solvent is an ether.

3. The process of claim 2 wherein said ether is tetrahydrofuran.

4. The process of claim 1 wherein said highly-electropositive metal is magnesium.

5. The process of claim 1 wherein the reduction of said bis-arene transition metal (I) compound is carried out at a temperature from about room temperature to about 150° C.

6. The process of claim 1 wherein the reduction is carried out at reflux temperature.

7. The process of claim 1 wherein the reduction of said bis-arene transition metal (I) compound is carried out with magnesium in the presence of tetrahydrofuran.

8. The process of claim 7 wherein said bis-arene transition metal (I) compound is a bis-arene compound of chromium, titanium or vanadium in a 1+ valence state, and wherein the arene is benzene, halogen-substituted benzene or benzene substituted with one or more alkyl groups containing from 1 to 6 carbon atoms.

9. The process of claim 8 wherein said bis-arene transition metal (I) compound is dibenzene vanadium (I) and the reduction is carried out at reflux temperature.

10. The process of claim 8 wherein said bis-arene transition metal (I) compound is bis(1,3,5-trimethylbenzene)vanadium (I) and the reduction is carried out at reflux temperature.

* * * * *